United States Patent
Felder

(10) Patent No.: US 11,730,582 B2
(45) Date of Patent: Aug. 22, 2023

(54) BARBED MESH FOR INCISION CLOSURE AND HERNIA REPAIR

(71) Applicant: John Felder, St. Louis, MO (US)

(72) Inventor: John Felder, St. Louis, MO (US)

(73) Assignee: Washington University, St. Louis, MO (US)

(*) Notice: Subject to any disclaimer, the term of this patent is extended or adjusted under 35 U.S.C. 154(b) by 464 days.

(21) Appl. No.: 17/031,133

(22) Filed: Sep. 24, 2020

(65) Prior Publication Data

US 2021/0085442 A1 Mar. 25, 2021

Related U.S. Application Data

(60) Provisional application No. 62/905,767, filed on Sep. 25, 2019.

(51) Int. Cl.
*A61F 2/00* (2006.01)

(52) U.S. Cl.
CPC .... *A61F 2/0063* (2013.01); *A61F 2002/0068* (2013.01); *A61F 2210/0004* (2013.01); *A61F 2220/005* (2013.01); *A61F 2220/0016* (2013.01); *A61F 2250/0018* (2013.01)

(58) Field of Classification Search
CPC ............ A61F 2/0063; A61F 2002/0068; A61F 2210/0004; A61F 2220/0016; A61F 2220/005; A61F 2250/0018; A61F 2002/0081; A61F 2220/0033; A61F 2250/006

See application file for complete search history.

(56) References Cited

U.S. PATENT DOCUMENTS

| | | | |
|---|---|---|---|
| 6,991,643 B2 * | 1/2006 | Saadat | A61F 2/4618 606/221 |
| 7,381,211 B2 | 6/2008 | Zamierowski | |
| 8,710,289 B2 | 4/2014 | Russell et al. | |
| 9,463,020 B2 | 10/2016 | Wilke et al. | |
| 2015/0057762 A1 * | 2/2015 | Harms | A61F 2/02 623/23.74 |
| 2015/0157440 A1 * | 6/2015 | Flynn | A61B 17/29 606/208 |
| 2016/0095597 A1 | 4/2016 | Belson et al. | |
| 2017/0319319 A1 * | 11/2017 | Fischer | A61B 17/064 |

* cited by examiner

*Primary Examiner* — Katherine M Shi
*Assistant Examiner* — Nasheha Baset
(74) *Attorney, Agent, or Firm* — Polsinelli, PC

(57) ABSTRACT

A barbed mesh device is provided for tissue closure and tissue support when the tissue is closed by other means. The device includes a macroporous mesh with a plurality of intersections or apertures and a plurality of barbs extending from the plurality of intersections or apertures on at least one side of the mesh. The plurality of barbs each include a barb body and a plurality of projections extending at an angle from the barb body.

16 Claims, 13 Drawing Sheets

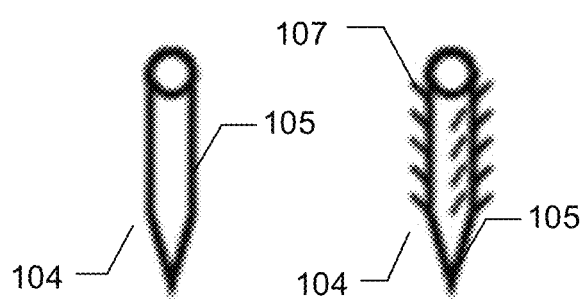
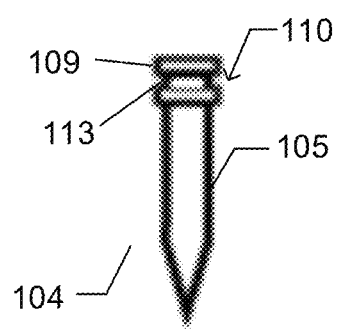
FIG. 9A  FIG. 9B  FIG. 9C
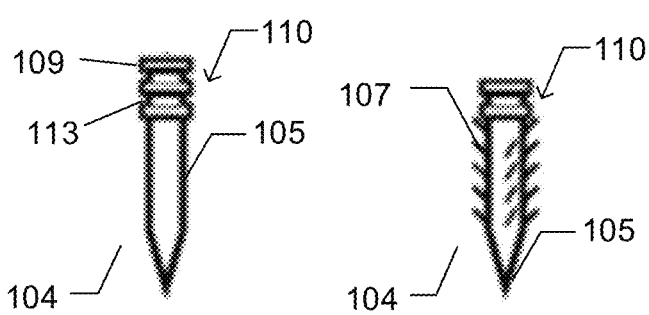
FIG. 9D  FIG. 9E  FIG. 9F

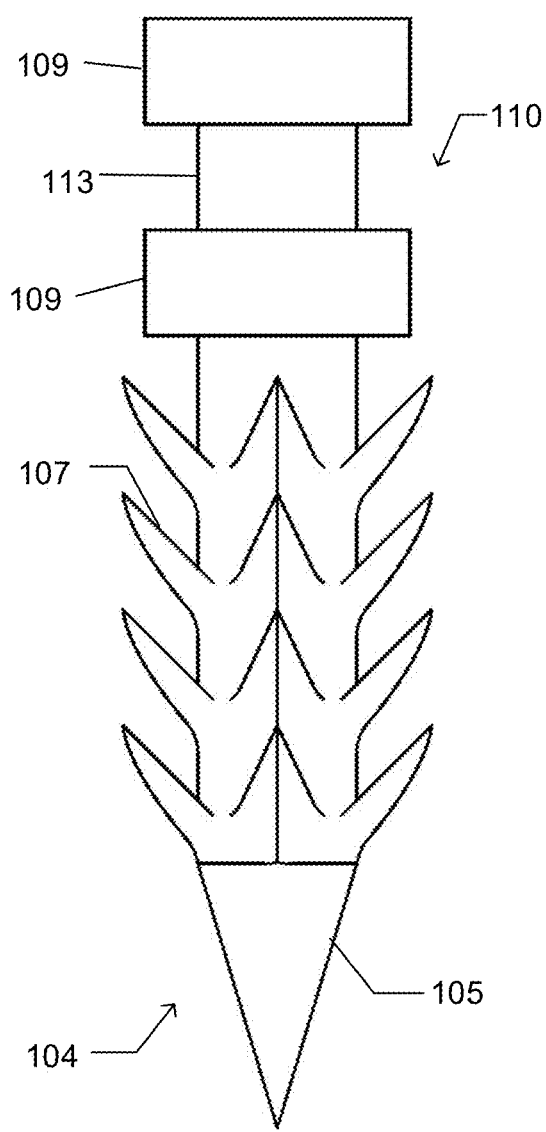
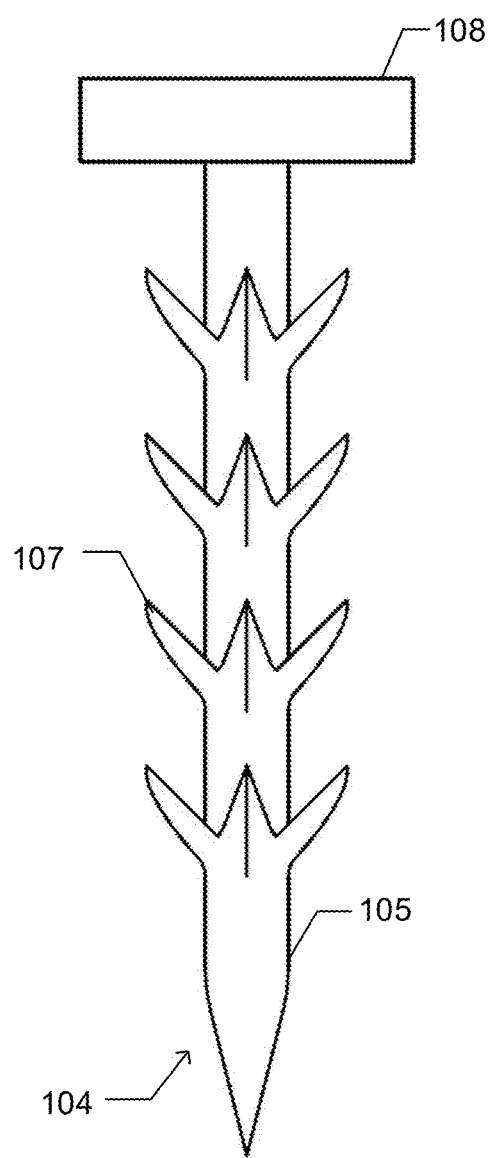
FIG. 9G    FIG. 9H

BARBED MESH FOR INCISION CLOSURE AND HERNIA REPAIR

CROSS-REFERENCE TO RELATED APPLICATIONS

This application claims priority under 35 USC § 119(e) to U.S. Patent Application Ser. No. 62/905,767, filed on Sep. 25, 2019, the entire contents of which are hereby incorporated by reference.

FIELD

The present disclosure relates generally to a barbed mesh for soft tissue closure and hernia repair. In at least one example, the present disclosure relates to a mesh with self-fixating barbs that may achieve tissue approximation and stability.

BACKGROUND

Closure of incisions with needle and thread is an ancient technology, and yet it remains the standard method of incision closure. Suture closure of wounds is time-consuming, operator-dependent in its outcome quality, and may require multiple layers of closure, doubling or tripling the effort and time needed for closure of a given length of incision. Suture closure of soft tissues subject to separating forces by large muscles (e.g. closure of abdominal wall fascia) has a significant rate of failure. Regarding abdominal fascia closure in particular, it has been thoroughly proven that traditional suturing techniques result in a higher incidence of hernia formation than techniques incorporating mesh. Many surgeons now prophylactically place mesh during abdominal fascia closure. However, use of a mesh itself still requires extensive suturing for placement.

As presented herein, a barbed mesh has been developed to aid in hernia repair or soft tissue closures without the need for sutures.

BRIEF SUMMARY

Provided herein is a device for tissue closure. The device may include a macroporous mesh including a plurality of intersections, the mesh having a first side and a second side; a plurality of barbs extending from the plurality of intersections on the first side of the mesh, the plurality of barbs each including: a barb body; and a plurality of projections extending at an angle from the barb body. In some aspects, the plurality of barbs may further extend from the plurality of intersections on the second side.

The device may be operable to close tissue transcutaneously, subcutaneously, or across fascial planes. The barbs may extend at an angle from about 10 degrees to about 170 degrees from the first side and/or the second side of the mesh. The plurality of barbs may be operable to penetrate and self-adhere to the tissue. The mesh and plurality of barbs may be biologically resorbable and may be made of polydioxanone, polypropylene, polyglecaprone, polyglactin, poly-4-hydroxybutyrate, and/or magnesium, titanium, or other metals. The plurality of intersections each have an aperture, such that each barb may be received within the aperture of a respective intersection. Each barb may further include a flat cap and/or at least one circumferential cuff to secure the barb in the aperture. Linking filaments may be connected to each of the plurality of barbs, such that a set spacing between each barb may be maintained as the barbs are connected to the apertures in the mesh. In some aspects, the mesh includes a portion without barbs. For example, the mesh may include an elastic portion.

Also provided herein is a device for tissue closure that includes a macroporous mesh that has a plurality of apertures, the mesh having a first side and a second side; a plurality of barbs operable to connect to the mesh, via the apertures, and extend from at least the first side of the mesh. The plurality of barbs each include: a barb body; a plurality of projections extending at an angle from the barb body; and a flat cap and/or at least one circumferential cuff to secure each barb in a corresponding aperture. In some aspects, the plurality of barbs further extend from the second side of the mesh. The barbs may extend at an angle from about 30 degrees to about 90 degrees from the first side and/or the second side of the mesh. The plurality of barbs may be linked together, via a linking filament, prior to being connected to the apertures in the mesh, such that a set spacing between each barb may be maintained when the barbs are connected to the apertures in the mesh.

Also disclosed herein is a method of tissue closure using the barbed mesh device. The method may include approximating edges of an opened tissue; placing a first side of the device over a broad surface area covering the edges of the opened tissue; and pressing on the device, wherein the barbs penetrate and are retained within the tissue. The placed device may be used to repair or prevent an abdominal hernia, close an incision in soft tissue, or support other methods of tissue closure to prevent dehiscence.

Other aspects and iterations of the invention are described more thoroughly below.

BRIEF DESCRIPTION OF THE DRAWINGS

Implementations of the present technology will now be described, by way of example only, with reference to the attached figures, wherein:

FIG. 9A shows an example modular locking barb without projections and without cuffs;

FIG. 9B shows an example modular locking barb with projections and without cuffs;

FIG. 9C shows an example modular locking barb without projections and with a single cuff;

FIG. 9D shows an example modular locking barb without projections and with two cuffs;

FIG. 9E shows an example modular locking barb with projections and with a single cuff;

FIG. 9F shows an example modular locking barb with projections and with two cuffs;

FIG. 9G shows an example modular locking barb with thick projections and a single cuff;

FIG. 9H shows an example modular barb with projections and a top cap;

DETAILED DESCRIPTION

Figure 1A:
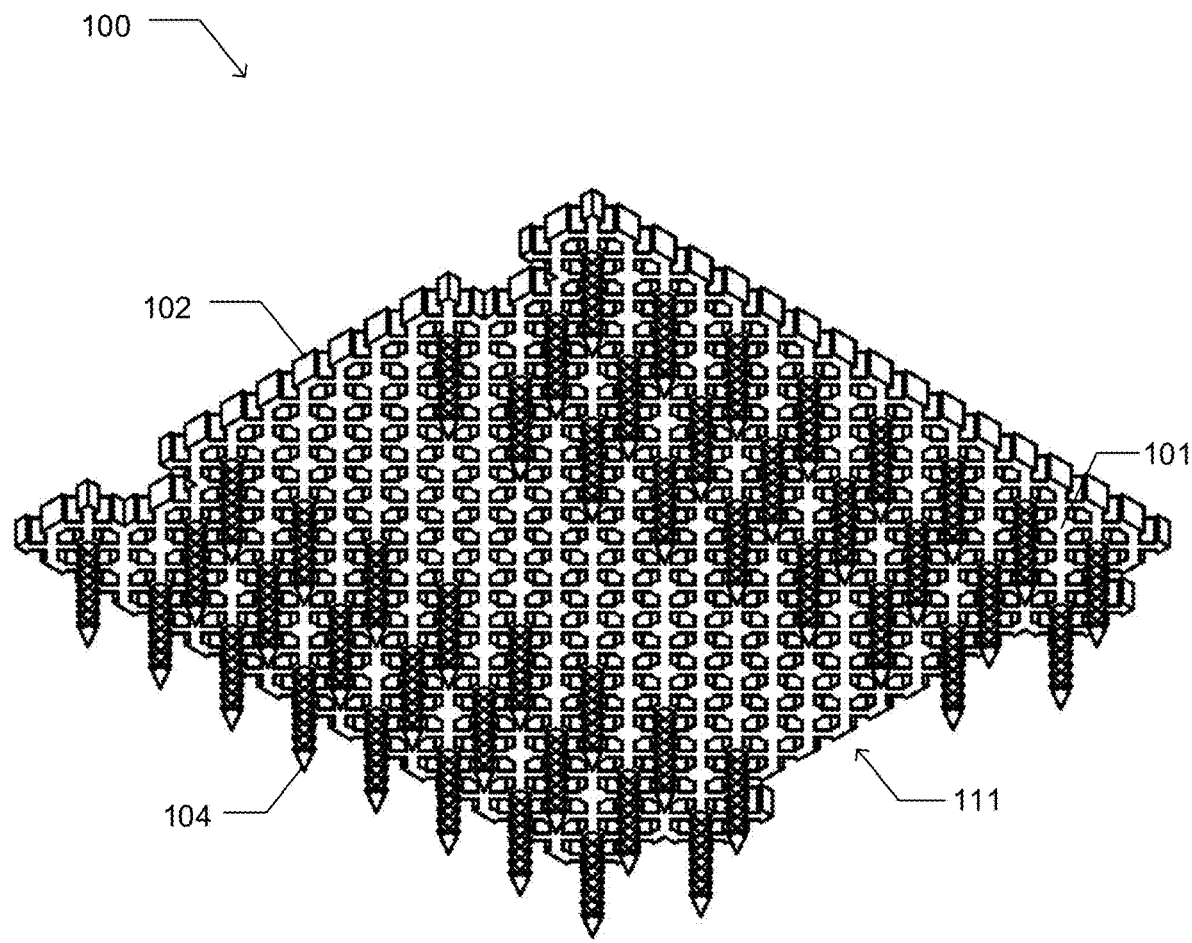
FIG. 1A is a perspective view of an example prefabricated barbed mesh for tissue fixation.
Figure 1B:
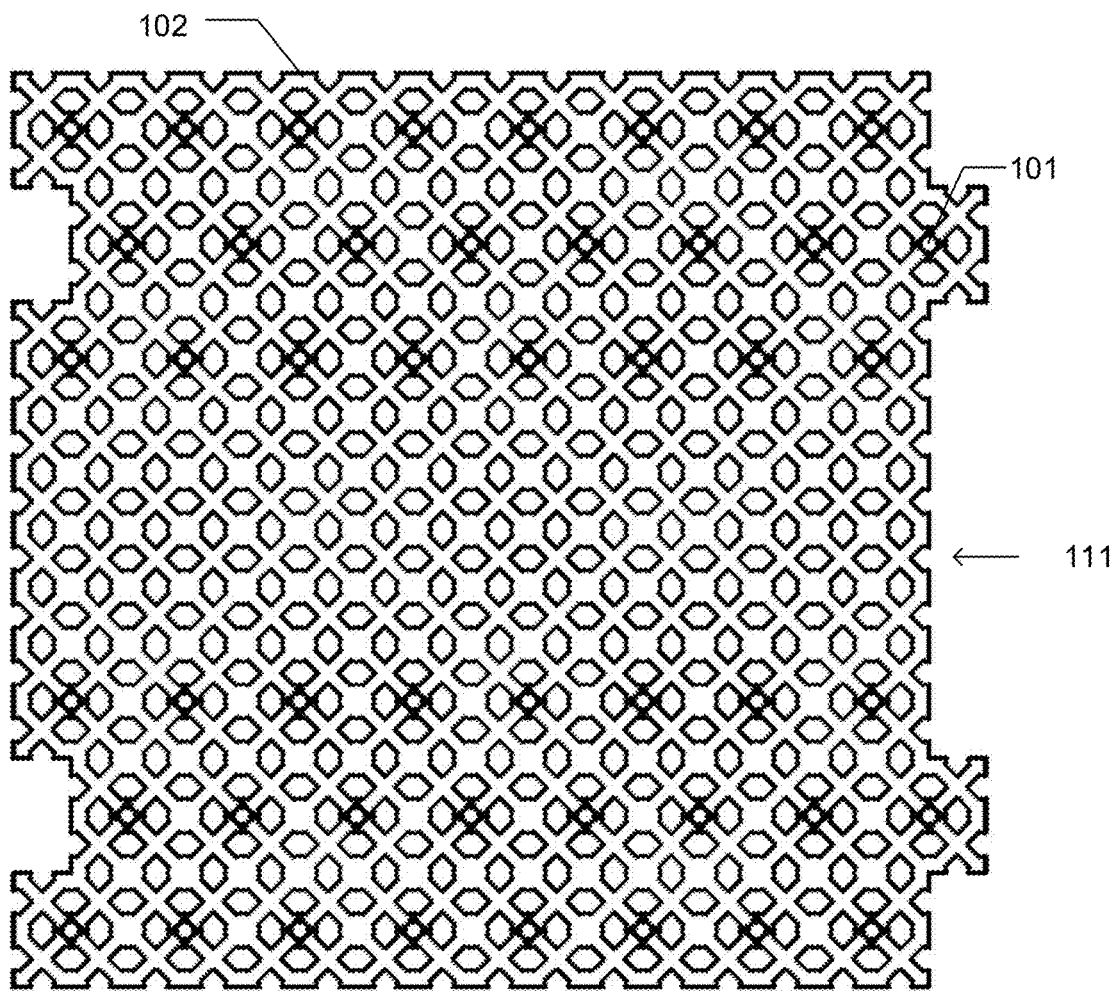
FIG. 1B is a top view of an example pre-fabricated barbed mesh for tissue fixation.
Figure 1C:
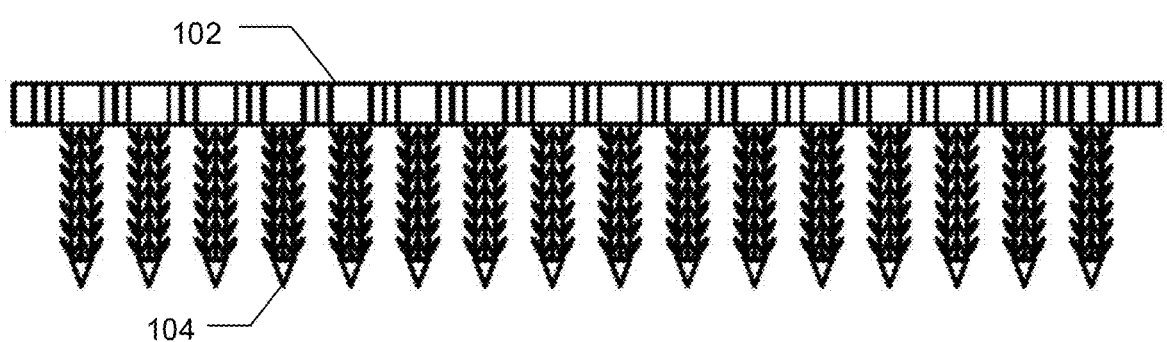
FIG. 1C is a side view of an example pre-fabricated barbed mesh for tissue fixation.
Figure 2:
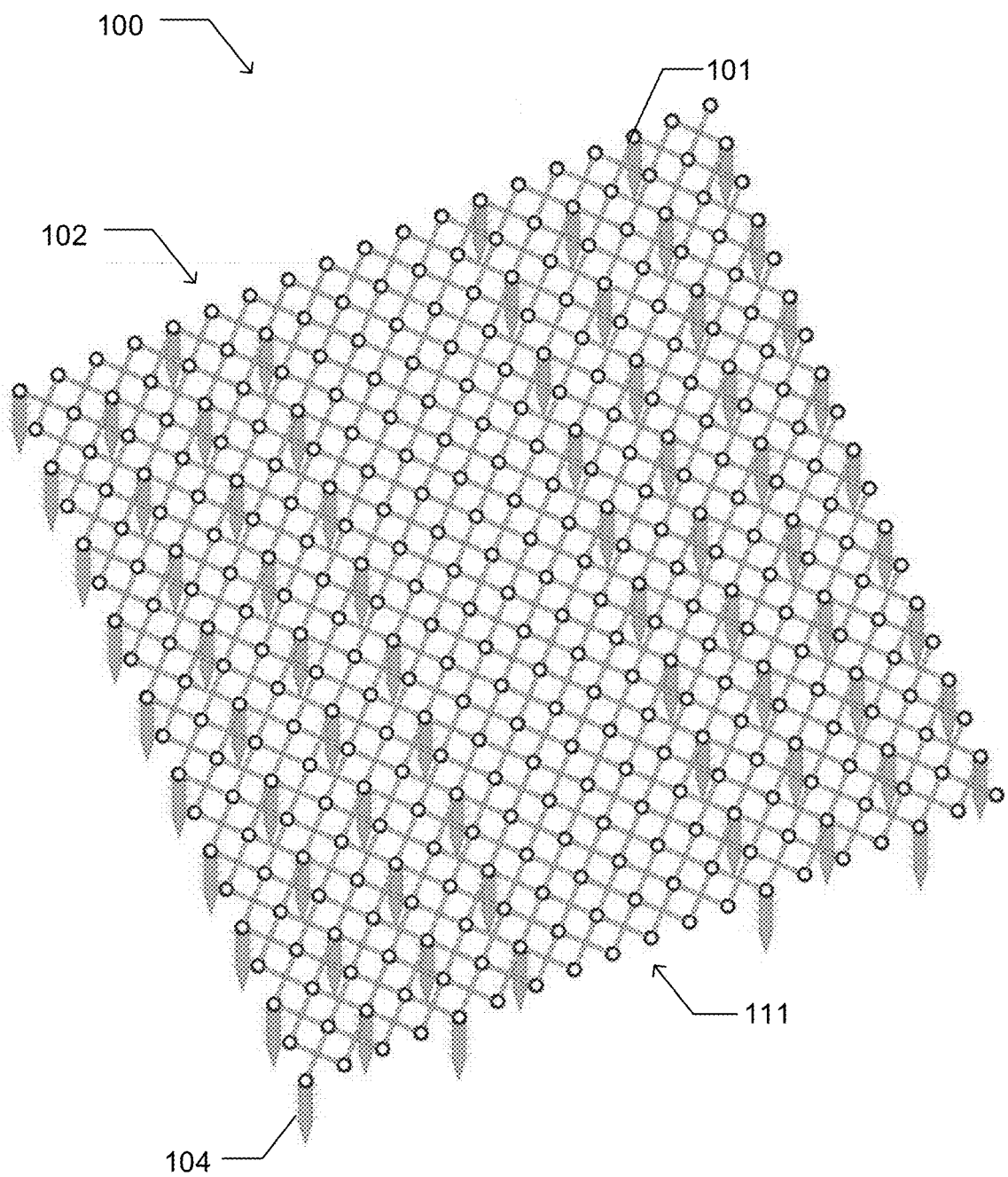
FIG. 2 is a perspective view of another example prefabricated barbed mesh.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof."

Generally, the ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc. Other than in the operating examples, or where otherwise indicated, all numbers expressing quantities of ingredients and/or reaction conditions may be modified in all instances by the term "about," meaning within +/−5% of the indicated number.

The terms "coupled" and "attached" are defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. The terms "comprising," "including" and "having" are used interchangeably in this disclosure. The terms "comprising," "including" and "having" mean to include, but not necessarily be limited to the things so described.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

Figure 3:
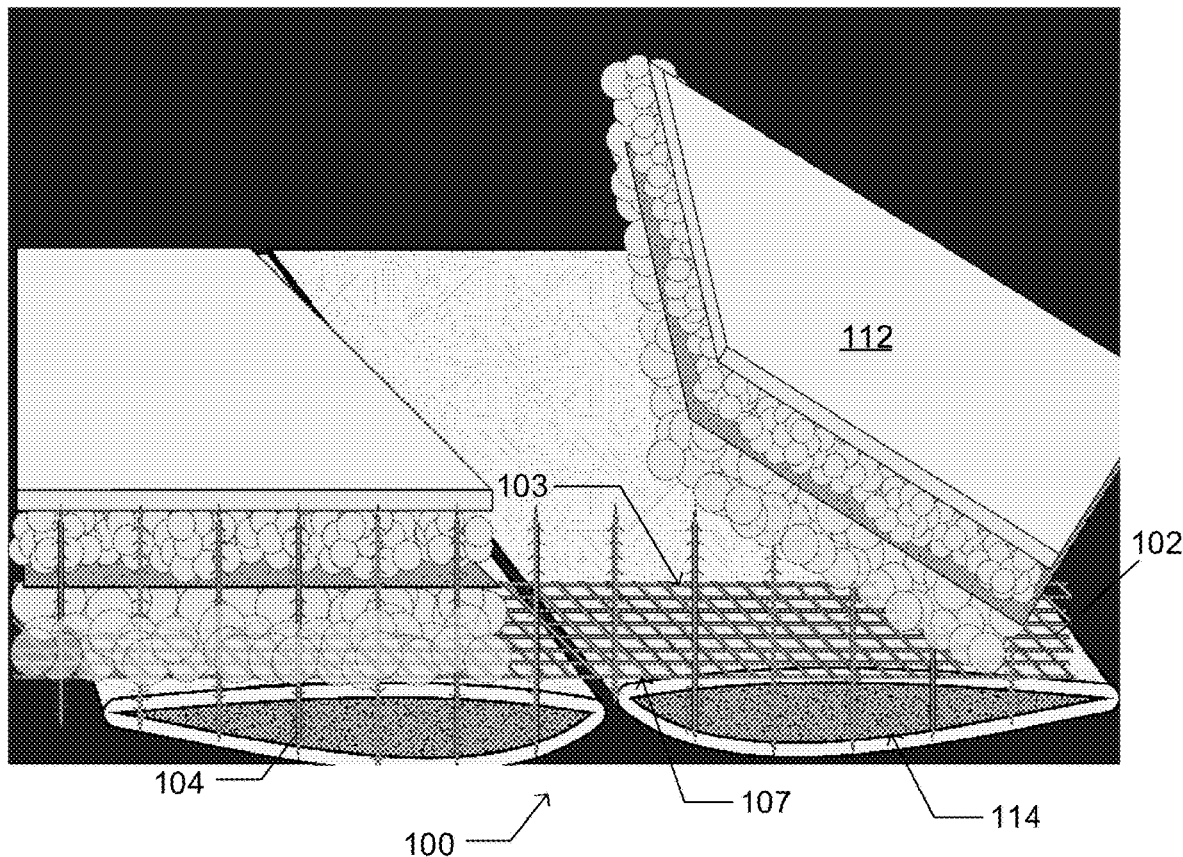
FIG. 3 shows an example barbed mesh with barbs on both sides, fixating overlying tissue planes to underlying tissue planes.

Provided herein is a barbed mesh device for wound closure for use as an alternative to sutures. The device is a mesh designed to stably fixate soft tissues in an approximated position, and does not require suturing for its application or stability. As seen in FIGS. 1A-1C and 2, the device may include a mesh with affixed barbs that penetrate and adhere to tissues. Alternatively, as seen in FIGS. 4A-8, the device may be modular with barbs that may be coupled to a mesh in a modular fashion to allow the surgeon to adapt the device to the particular patient and/or the particular use (i.e. soft tissue closure, reinforcement, hernia repair, etc.). The barbed mesh allows rapid, 'single iteration' fixation of multiple layers of soft tissues, for example as seen in FIG. 3, as opposed to sutures which require tens of iterations of the same movement. It various examples, the barbed mesh may be used for subcutaneous or transcutaneous skin closure, abdominal fascial closure, closure across fascial planes, and other surgical applications.

The barbed mesh with self-fixating barbs may achieve tissue approximation and stability without the wasted time and variability of suturing. In some examples, the barbed mesh may reduce operating room time, reduce effort required to complete repetitive or mundane portions of procedures, and reduce complications such as wound dehiscence or hernia repair that are associated with mechanical limitations of traditional sutures.

The barbed mesh provides broad, 2 and 3-dimensional fixation of tissues which may impart inherent stability and distribute tension and tissue injury away from wound edges, where healing is critical. Without being limited to any one theory, insertion of the barbs may not cause local tissue ischemia, as sutures do. The barbed mesh is a load-bearing construct, such that the barbs transmit tension and distracting forces from tissue into the mesh, allowing the mesh to bear the tension of tissue closure.

The barbed mesh may have significant advantages over traditional sutures, as a single-step application would close an entire incision, replacing the need for multiple sutures. The tendency for "Cheesewiring" would be reduced or eliminated in the same way it is with use of any mesh. Multiple tissue planes (e.g dermis, subcutaneous fat, superficial fascia) may all be approximated with one application (e.g. with barbs the penetrate deeply), as opposed to devices such as staples that only approximate the dermis but allow deeper layers of tissue to pull away from one another. The cumulative time savings in the operating room would be significant during a day, week, or month, and would themselves amount to a financial resource, as OR time is very expensive. It would expedite the process of wound closure, reduce operator variability, and, potentially, reduce the likelihood of dehiscence or hernia formation by incorporating broad mesh fixation at the time of primary closure.

As seen in the figures, the barbed mesh 100 includes a flexible, large pore (macroporous) mesh 102 as the base of the device with a plurality of penetrating barbs 104. In some examples, such as in FIGS. 1A-1C and 2, the barbed mesh is pre-fabricated with the barbs integrally and rigidly connected to a plurality of intersections 101 in the mesh. Not every intersection 101 includes a barb. The barbs of the barbed mesh may extend from a first side and/or a second side (i.e. bidirectional barbs). With integrated bidirectional barbs, the barbs on one side may originate from the same or different intersections as barbs on the other side.

In other aspects, the barbed mesh 100 may be modular such that the mesh 102 and plurality of barbs 104 are manufactured separately and the barbs 104 may be connected to the mesh 102 by a user in a modular fashion. In some examples, the mesh 102 may have apertures 106 in the linkage points/intersections 101 of the mesh, each aperture 106 operable for receiving a barb, for example as seen in FIGS. 4A-8.

The mesh may have a generally square, rectangular, circular, or oval shape. The mesh may be provided in multiple sizes, and also be able to be "cut to fit," such that a larger piece can be cut to fit a smaller need. For abdominal hernia repair, the mesh may range from about 5×10 cm to about 30×35 cm. For transcutaneous skin closure, the mesh may have a width of about 2 cm to about 10 cm, and the length of the mesh may be about 5 cm, up to about 10 cm, up to about 15 cm, up to about 20 cm, up to about 30 cm, up to about 40 cm, up to about 50 cm, or any length needed for covering the opening. In at least one example, the mesh may be about 20 cm×30 cm. In other examples, the mesh may be provided as a roll where a length of the mesh can be taken from the roll and cut as needed. In this example, the surgeon may determine the length of the mesh. The mesh may have a thickness ranging from about 0.1 mm to about 5 mm. In some examples, the mesh may have a thickness of less than about 0.1 mm, at least about 0.1 mm, at least about 0.5 mm, up to about 0.5 mm, at least about 1 mm, up to about 1 mm, at least about 2 mm, up to about 2 mm, at least about 3 mm, up to about 3 mm, at least about 4 mm, up to about 4 mm, at least about 5 mm, or up to about 5 mm.

The barbed mesh 100 may be used to close separated tissue and the barbs may extend from one or both sides of the mesh, depending on the application. In some aspects, for example as seen in FIGS. 1A-1C and 2, the barbs 104 may extend only from a first side of the mesh 102. The mesh 102 may have a tissue facing side 103 with barbs 104 that contact to tissue and an external facing side 105 that is exposed to the air or further covering when the barbed mesh 100 is used transcutaneously. In some examples, a dry gauze dressing or a transparent film dressing may be placed over the barbed mesh for about 2 days until the incision has re-epithelialized. In other examples, as seen in FIG. 3, the barbs 104 may extend from a first and second side of the mesh 102. When barbs are on both sides of the mesh, the opposing barbed surfaces may be used to, for instance, fixate two layers of tissue that are deep/superficial to one another. In one example, a barbed mesh 100 with bidirectional barbs 104 such that barbs extend both down from the mesh 102 and up from the mesh 102 to allow fixation of fascia below the mesh and subcutaneous tissue above the mesh with a single barbed mesh 100 device to fixate elevated/undermined flaps of subcutaneous tissue to the fascia beneath it, eliminating shearing and dead space. The mesh 102 may have a first side (i.e. tissue facing side) 103 and a second side (i.e. a fascia facing side) 107, with barbs 104 projecting outward from both sides when the barbed mesh 100 is used subcutaneously, transfascially, or subfascially. The first side 103 may contact and penetrate the tissue 112, and the fascia facing side 107 may either face an overlying superficial tissue plan 114 (e.g. subcutaneous tissue deep surface or potential space created by elevation of a subcutaneous tissue flap) or a body cavity (e.g. the peritoneal space). When used in these positions, the mesh may also have two sides with barbs, each facing and intended to penetrate different tissue layers. In this example, the bidirectional barbs 104 extend up from the mesh 102 towards the subcutaneous tissue 112 and down from the mesh 102 towards the fascia 114.

The barbed mesh may be permanent or biologically resorbable with varying tensile strength and elasticity/rigidity characteristics for various applications. In at least one example, the mesh is biodegradable. The mesh and/or barbs may degrade after a period of time long enough for the tissue to have healed and the mesh is no longer needed for closure/repair. For abdominal fascia repair, the mesh may be made of polydioxanone, polypropylene, polyglactin, polyglecaprone, and/or poly-4-hydroxybutyrate. For skin closure or permanent/removable uses, the mesh may be made of polypropylene, as polypropylene has minimal reactivity. The barbs in this case would be composed of either polypropylene, or resorbable material such as polyglactin, polyglecaprone, polydioxanone, or something similar. In some instances, parts or all of the mesh and/or barbs may also be coated with, constructed with, or contain metals, such as magnesium, titanium, stainless steel or its associated alloys, and/or other biologically resorbable metals to impart certain rigidity, tissue penetration, and handling characteristics. In various examples, the mesh may have a tensile strength of at least about 20 Newtons.

Referring to FIGS. 1A-1C and 2, the mesh may include a central portion 111 or stripe that is absent of any barbs. In some examples, the central portion or stripe may incorporate an elastic zone to aid tissue approximation. The central portion may be between about 1 cm and 3 cm in width, and span the length of the mesh, overlying the incision to be closed. In at least one example, the central portion is about 2 cm wide. Non-limiting example materials include rubber, silicone, and/or materials with a different elastic modulus than the rest of the mesh. Other methods of achieving elasticity include including structural differences in portions of the mesh, such as altering the fibers of the mesh from a linear shape to a serpentine, helical, or coiled shape that may have an innate tendency to recoil. The central line of the mesh, overlying the incision may also have an open window (e.g. a strip of about 1-3 cm in width in the center of the mesh with no mesh/material) that would allow the operator to pass an instrument through to grab the fascia or skin edge and pull it towards the center of the mesh.

Figure 4A:
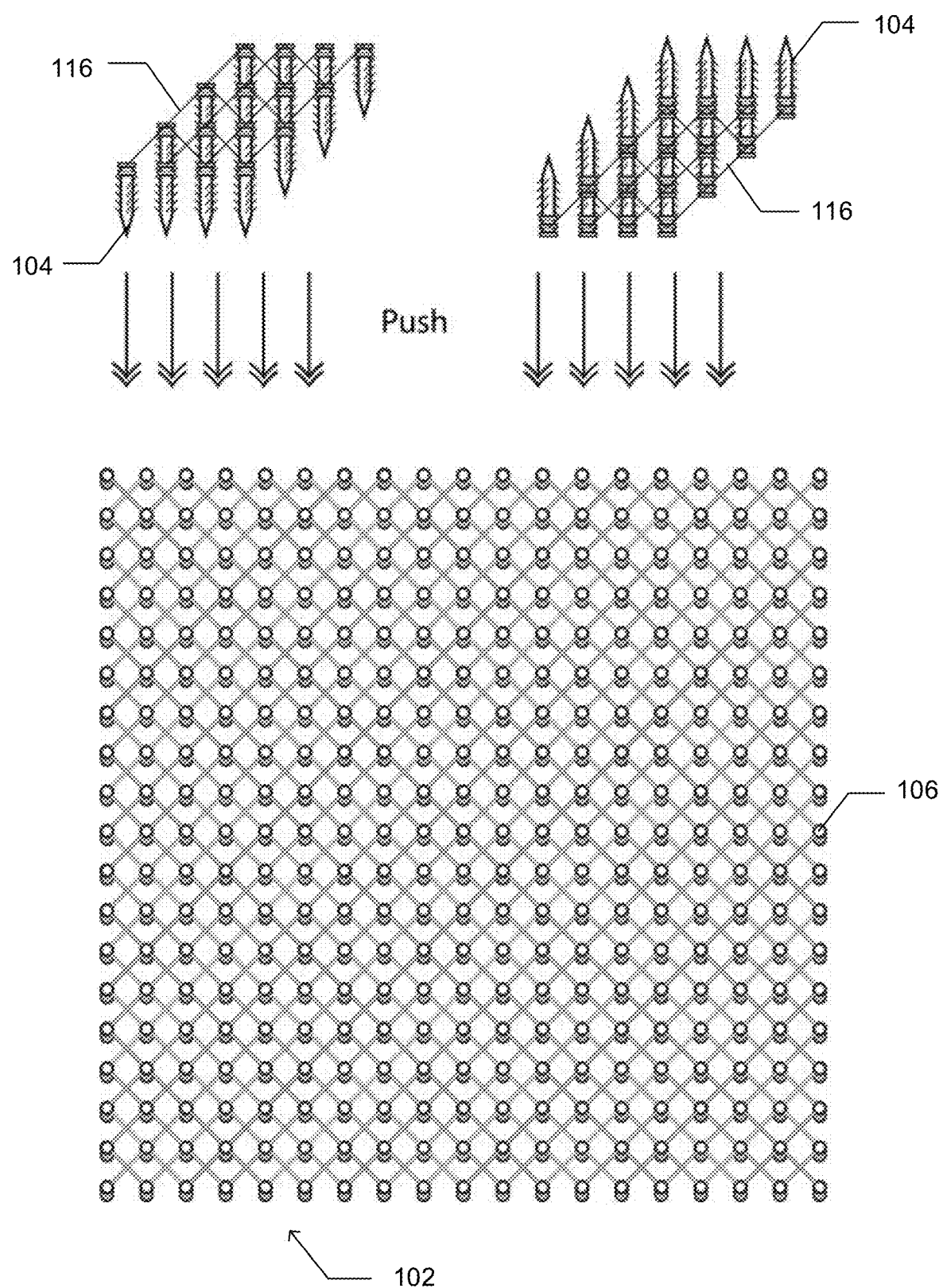
FIG. 4A is an example modular mesh platform with linked locking barbs.
Figure 4B:
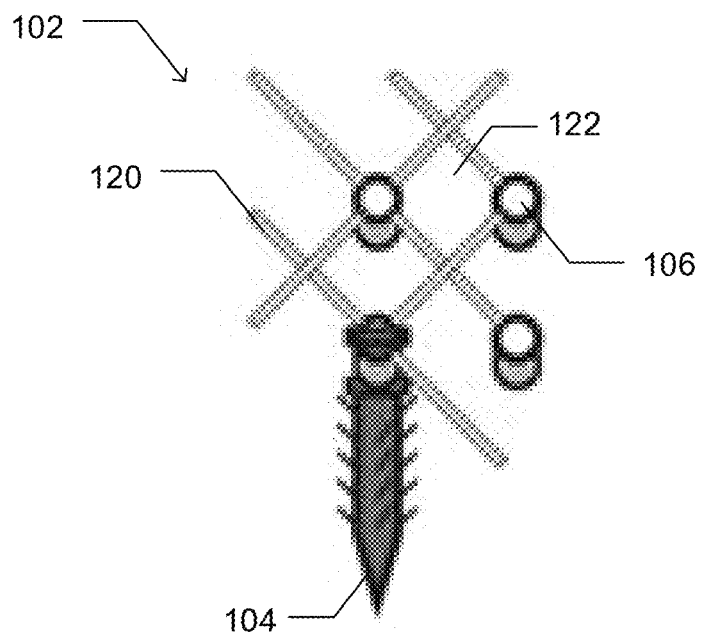
FIG. 4B is an example barb with a cuff inserted into an aperture of a modular mesh.
Figure 4C:
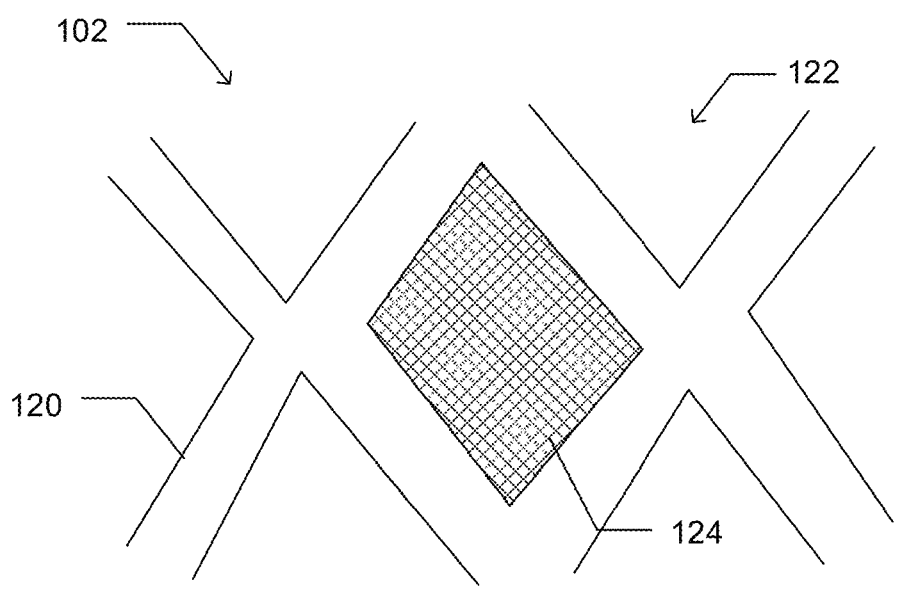
FIG. 4C is an example mesh with a fine weave mesh within a pore of the mesh.

The mesh may have a lattice-like structure with mesh fibers 120 that cross to form large pores/interstices 122 between the intersections 101 and/or apertures 106, as seen in FIGS. 4B and 4C. In some examples, the pores 122 of the load bearing mesh 102 may be filled with a finer weave 124 of the mesh fibers to increase the surface area of the barbed mesh for tissue integration. In other examples, a second layer (e.g. overlay) of a woven mesh may be attached to a first layer (e.g. underlying load-bearing mesh construct). The two layers may be joined by an adhesive, by snaps, or by apertures or barbs from one mesh, or by any other means for joining two meshes.

Attached or connected to the mesh are a plurality of rigid or semi-rigid barbs 104 that penetrate and self-adhere to tissue. The barbs are operable to allow the mesh to bear the strain of tissue closure by translating mechanical strain from the tissues to the mesh itself, resisting distracting forces at the site of tissue healing. For example, the barbs are designed to ensure abdominal wall tissue is penetrated but not severed. The barbs may be integral with the mesh or may be modularly connected to the mesh. The barbs may extend from one or both sides of the mesh. For example, the barbs may cover the tissue facing side of the mesh and/or the fascia facing side of the mesh. The barbs may be evenly spaced, randomly spaced, or spaced in a pattern over a surface of the mesh.

As seen in FIGS. 9A-9H, the barbs 104 may include a barb body 105 and one or more projections 107 or smaller sub-barbs emanating from the barb body. The barb body may have a shaft portion and a taper portion ending at a point at one end that is sufficient to pierce tissue. Projections 106 may be extend from the shaft portion of the barb body 105. In some examples, the projections from the barb body may allow for the barb to be securely fixated in the tissues and provide resistance to pull out the barb from the penetrated tissues. In some instances, the barbs may be free of projections (e.g. FIGS. 9A, 9C, and 9D) to facilitate tissue penetration or make the device removable for positioning purposes. The barbs may be used in various quantities and concentrations on the mesh.

The barbs and projections may vary in type, quantity, thickness, length, angle, shape, spacing, or direction with various projection configurations (or be smooth, without projections), for various indications. For example, the barbs may be round, triangular or rectangular/prism-shaped, blade-like, curved, tooth-like, or may assume other similar forms. For example, the barbs may have a shape that allows tissue to be penetrated but not severed. The apertures within the mesh may be similarly shaped as the barb to facilitate receiving and locking the barb within the aperture. The barbs may have a shape to optimize the stability of the barbs and the strength of their attachment to the mesh, for instance, the barbs may be wider at their base where they project from the mesh and taper to a smaller diameter at the point of the barb to facilitate tissue penetration. The barbs may be angled, such that the portion of the barb that interfaces with the modular mesh platform is perpendicular to the mesh, but the barb is then bent or angled such that it projects from the mesh at a non-perpendicular angle.

The barbs may have a length ranging from about 0.1 cm to about 15 cm. For example, the barbs may have a length of about 0.5 cm, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm. In at least one example, the barbs may have a total length of about 7.5 mm, with about 5 mm being the shaft of the barb body and 2.5 mm being the taper to the point at the end of the barb. The barbs may have a diameter ranging from about 0.1 mm to about 3 mm. For example, the barbs may have a diameter of about 0.1 mm, about 0.5 mm, about 1 mm, about 1.5 mm, about 2 mm, about 2.5 mm, or about 3 mm. In at least one example, the barbs have a diameter of about 1.5 mm. The barbs may have variable lengths and diameters depending on the application for the barbed mesh. The operator may choose the appropriate length and diameter based on the particular patient and situation at hand. For example, closing the skin and subcutaneous fat of a patient with a BMI of 25 would require shorter length barbs (i.e. about 0.5-1 cm) while a patient with a BMI of 40 may require longer length barbs (i.e. about 5-10 cm).

The projections may be macroscopic, shaped projections, or may be a textured surface added to the barb body by e.g. cutting or coating with another material) that serves to generate resistance to pull-out. In some examples, the projections may be about 0.5 mm to about 2 mm in length. In at least one example, the projections may be about 1 mm long. The projections may extend at about 15 degrees to about 90 degrees from the barb body. In at least one example, the projections may extend at a 45 degree angle from the barb body. The barbs and projections function to transmit tension within the tissues into the mesh, which then becomes load bearing and resists separating forces on the tissues. In some examples, this may be achieved by making the barbed mesh rigid or semi-rigid. In some examples, the barb projections may be cut into the material of the barb body. In additional examples, the barb body may be fabricated by, for example, an injection mold technique, 3D printing, stereolithography, or laser-cutting. The projections may be created by the same methods as the barb body, by subtraction or precipitation, or by coating with a material generating a roughened surface. The projections may be macroscopic, shaped projections as depicted in the figures, or may be a textured surface added to the barbs by, for example, cutting, rasping, or coating (with another material) which serves to generate resistance to pull-out as the macroscopic shaped projections would.

In at least one example, the barbs and projections are biodegradable. The barbs may degrade after a period of time long enough for the tissue to have healed and the barbs are no longer needed for closure/repair. In some examples, the barbs and/or projections may be made of polydioxanone (PDS), polypropylene (e.g. Prolene), poly-4-hydroxybutyrate, vicryl (polyglactin), and/or monocryl (polyglecaprone). The barbs can be, but are not required to be the same material as the mesh. In one example, the barbed mesh may include a PDS mesh with PDS barbs, for abdominal fascia. In another example, the barbed mesh may include a Prolene mesh with Prolene barbs for abdominal applications. In yet another example, a Prolene mesh with PDS or monocryl barbs may be used. For skin, the barbed mesh may include a prolene mesh with penetrating monocryl (polyglecaprone) or PDS barbs. This combination would allow the barbs to disintegrate within a few weeks, allowing the external mesh to be peeled away and discarded when the incision is healed. Likewise, the projections may be fabricated in a variety of materials that may differ from both the barb body and the mesh. For example, in a trans-cutaneous application, the mesh and barb body may be polypropylene to reduce tissue reactivity, but the projections may be composed of polyglactin or a similar material that is quickly biologically degraded, allowing both the mesh and barbs to be pulled free of the sub-barbs and skin within a few weeks.

The barbs may be connected to attachment points on the mesh. In some examples, the penetrating barbs may be connected to apertures 106 and/or intersections 101 of the mesh. The barbs may be integral with the mesh or may be manufactured separately and attached to the mesh modularly. In some examples, the barbs may be connected to the mesh and project at an angle ranging from about 10 degrees to about 170 degrees, about 10 degrees to about 50 degrees, about 20 degrees to about 60 degrees, about 30 degrees to about 70 degrees, about 40 degrees to about 80 degrees, about 50 degrees to about 90 degrees, about 60 degrees to about 100 degrees, about 70 degrees to about 110 degrees, about 80 degrees to about 120 degrees, about 90 degrees to about 130 degrees, about 100 degrees to about 140 degrees, about 110 degrees to about 150 degrees, about 120 degrees to about 160 degrees, or about 130 degrees to about 170 degrees from the surface of the mesh. In at least one example, the barbs may be at a 30 degree to 90 degree angle from the surface of the mesh. For instance, the barbs may be angled towards an incision to aid in overcoming distracting forces and approximating the tissue. In at least one example, the barbs may extend from one or two sides of the mesh at a 90 degree angle from the surface of the mesh.

When the device is modular, the mesh may be a platform or base into which barbs can be mated or configured to suit various needs. For example, each barb may include one or more cuffs, slots, threads, caps, or other mating mechanism for interfacing with reciprocal cuffs, slots, ridges, threads, or mating mechanism in each aperture of the mesh to create a modular barbed mesh platform. The one or more cuffs, slots, threads, caps, or other mating mechanism on the barbs may be located on an end of the barb body. For example, the one or more cuffs, slots, threads, caps, or other mating mechanism may be at an end of the barb body opposite to the point of the barb. Referring to FIGS. 9A-9H, the barbs 104 may further include a flat cap 108 and/or at least one cuff 110 around the circumference of the barb body 105 to facilitate seating and securing each barb within an aperture 106 of the mesh 102 when the barbs are modularly connected to the mesh. The at least one cuff 110 may be formed by two or more flanges 109 extending from at least a portion of the circumference of the barb body 105 and a slot 113 between the two or more flanges 109. The flanges have a diameter wider than the diameter of the rest of the barb body. In some examples, the flanges may have a diameter of about 2 mm to about 3 mm. In at least one example, the flanges may have a diameter of about 2.5 mm. The flanges may have a thickness of about 0.5 mm to about 1.5 mm. In at least one example, the flanges have a thickness of about 1 mm. The barb may include 1, 2, 3, or more flanges. The slot, or space between flanges, may be about 0.5 mm to about 2 mm thick and may have the same diameter as the barb body. In at least one example, the flanges may be separated by about 1 mm. The barb may include 1, 2, 3, or more cuffs for securing the barb into a corresponding aperture. The barb may include two cuffs (i.e. 3 flanges) to allow reversible barbs. In some examples, the aperture may include at least one ridge shaped to securely fit within the slot of the cuff. In other examples, the aperture may be threaded to accept a barb with a corresponding threading. A cap may have a diameter wider than the diameter of the aperture, such that the cap prevents the barb from pulling completely through the aperture. The aperture and/or cuff may be operable to secure or fix each barb to the mesh.

Figure 5:
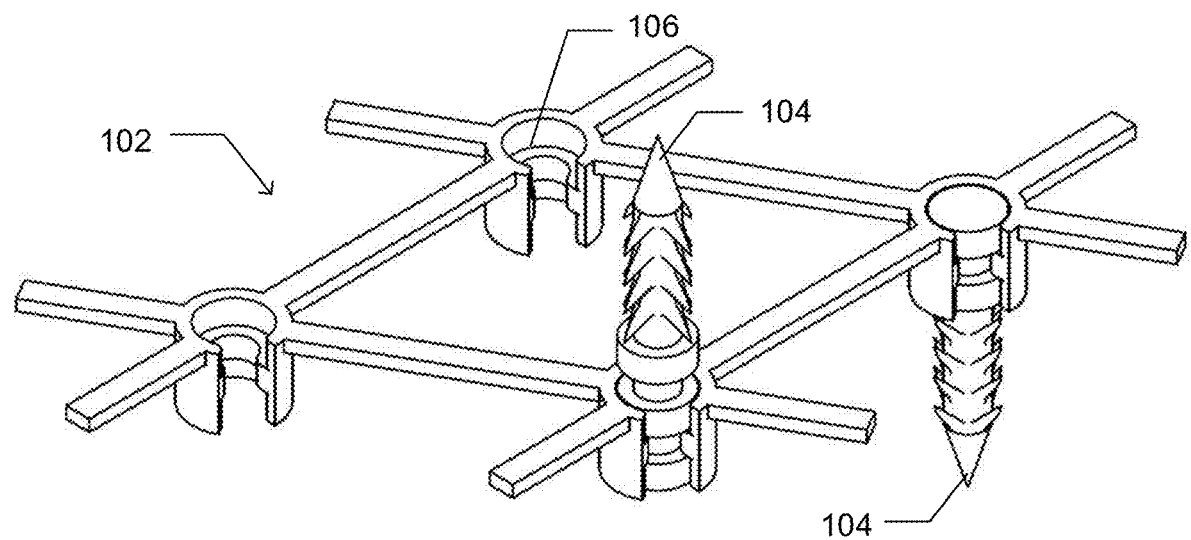
FIG. 5 shows an example modular mesh with semi-open cuffed apertures and cuffed/flanged barbs within the apertures.
Figure 6:
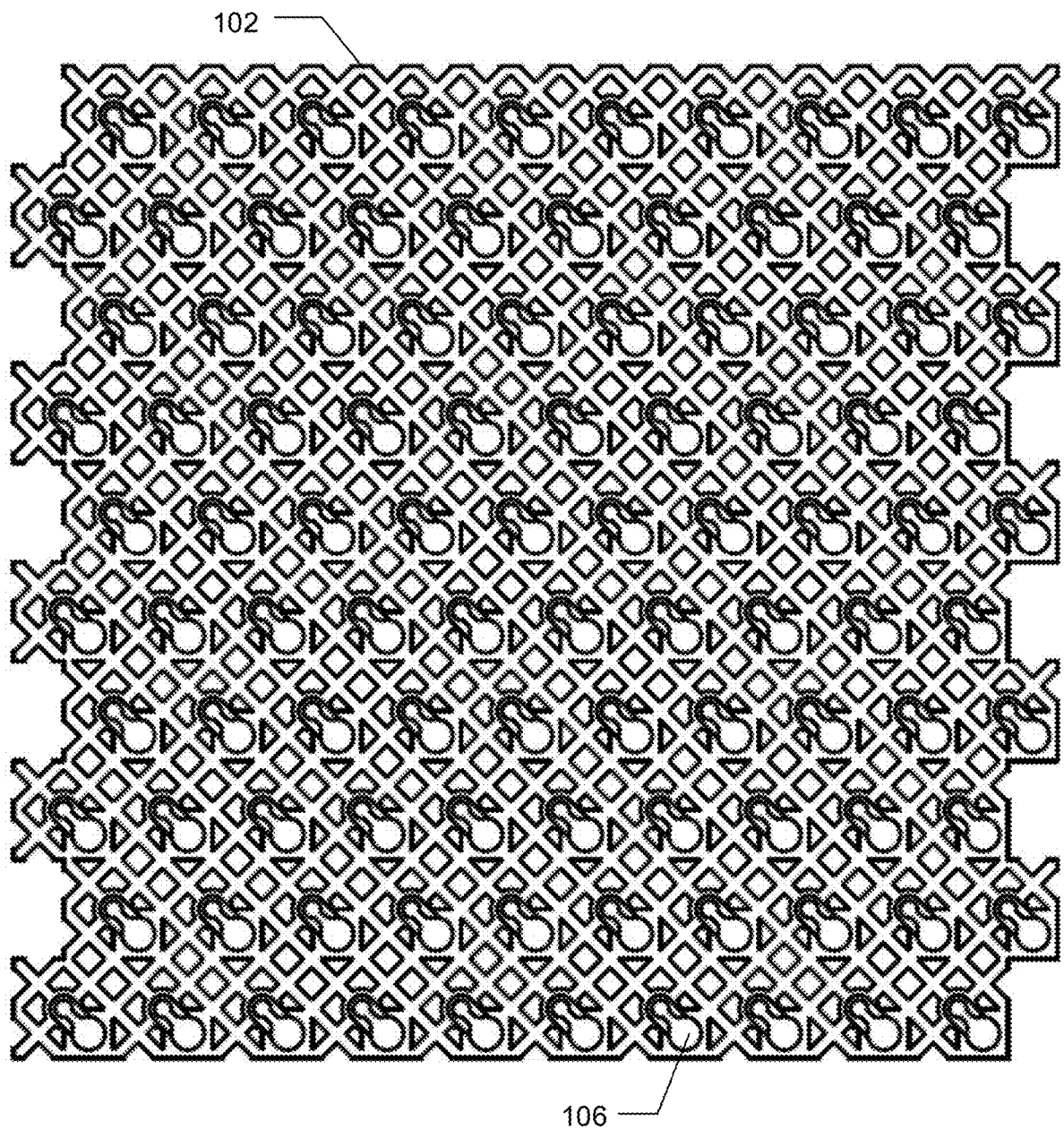
FIG. 6 shows an example modular mesh with apertures having slots.
Figure 7A:
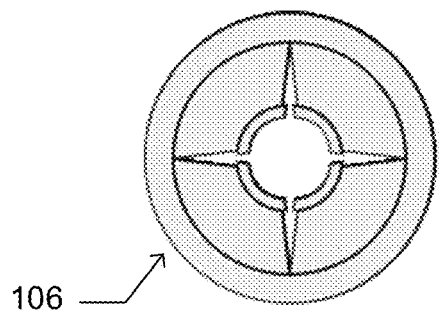
FIG. 7A is a top view of an example expandable basket/hoop aperture in a modular mesh.
Figure 7B:
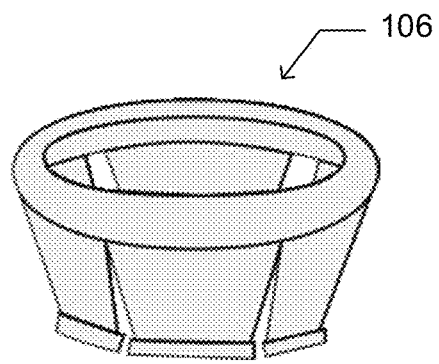
FIG. 7B is a perspective view of an example expandable basket/hoop aperture in a modular mesh.
Figure 7C:
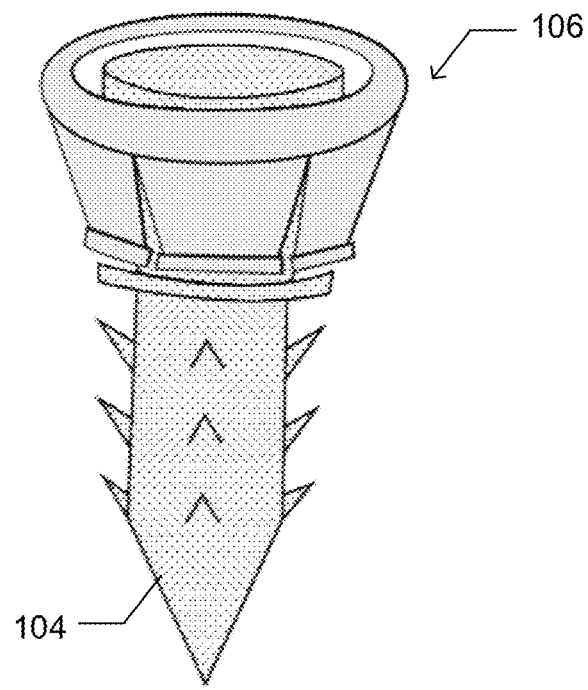
FIG. 7C is a perspective view of an example expandable basket/hoop aperture in a modular mesh with a connected barb.
Figure 8:
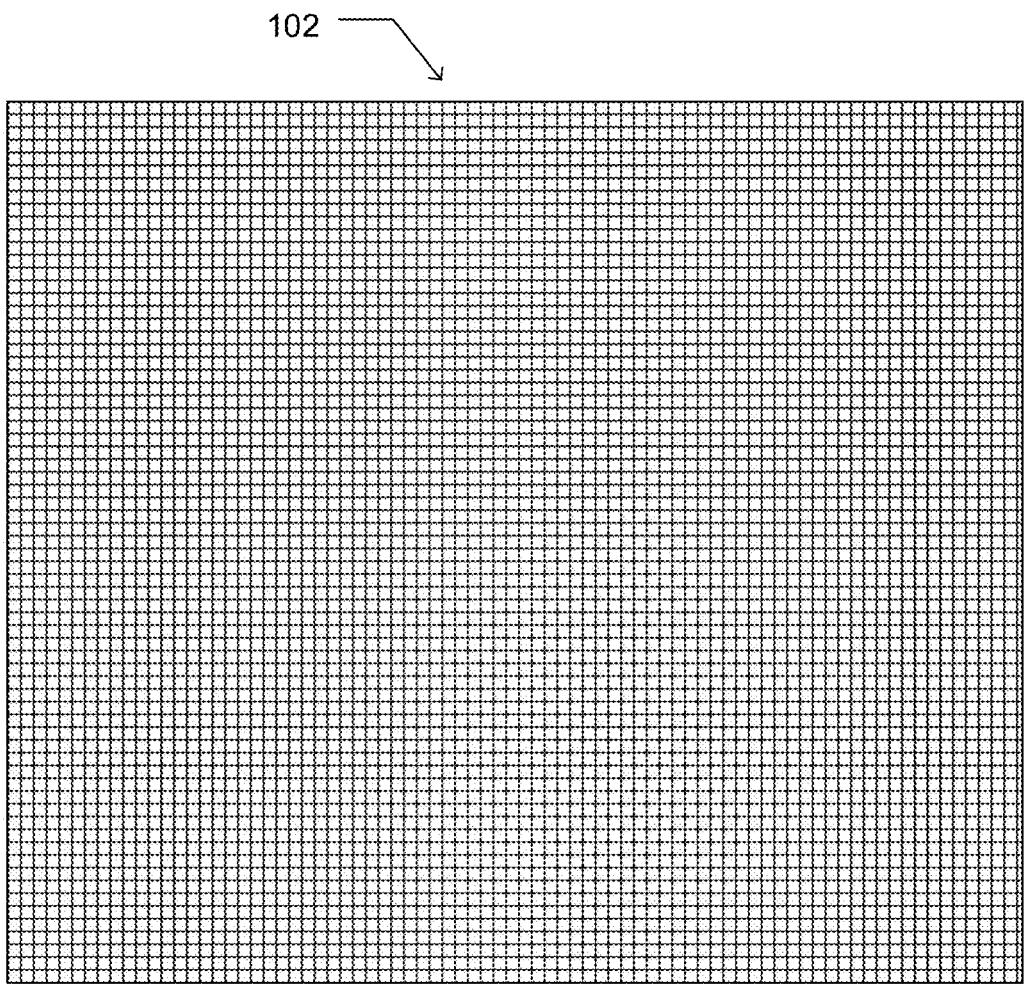
FIG. 8 is an example mesh with large apertures for receiving a barb with a cap.

The mesh may be arranged as a grid or otherwise patterned arrangement of apertures or intersections. In an example, the aperture may be a circular opening. The aperture may have a diameter sufficient to receive a barb, such as a diameter of about 1 mm to about 3 mm. In at least one example, the aperture has a diameter of about 1.75 mm. The aperture may further have a thickness sufficient to securely hold a barb, such as a thickness of about 0.5 mm to about 2 mm. In at least one example, the aperture may have a thickness of about 1 mm. In some examples, the aperture may constitute a three-quarters circle or other incomplete circle to allow expansion of the aperture to receive a barb having a diameter the same as the unexpanded aperture (FIG. 5). In additional examples, the aperture may contain a slot, with an aperture larger than the cuff of the barb to permit passage of the barb into the plane of the mesh, and then a slot with a width equal to the diameter of the barb, that would allow the barb to be slid into a secure position within the mesh (FIG. 6). In other examples, the aperture may be an expandable basket/hoop aperture. The expandable basket/hoop aperture may contain petal-like projections, angled out of the plane of the mesh by between 5 and 90 degrees that are operable to expand to allow passage of the barb, and then block backwards passage of the barb by making contact with the cuff of the barb (FIGS. 7A-7C). In yet additional examples, the apertures may be large pores arranged in a grid (FIG. 8). There may be further related mechanisms of joining the barbs to the mesh platform that are not specifically describe herein but function to achieve the same purpose.

Figure 10A:
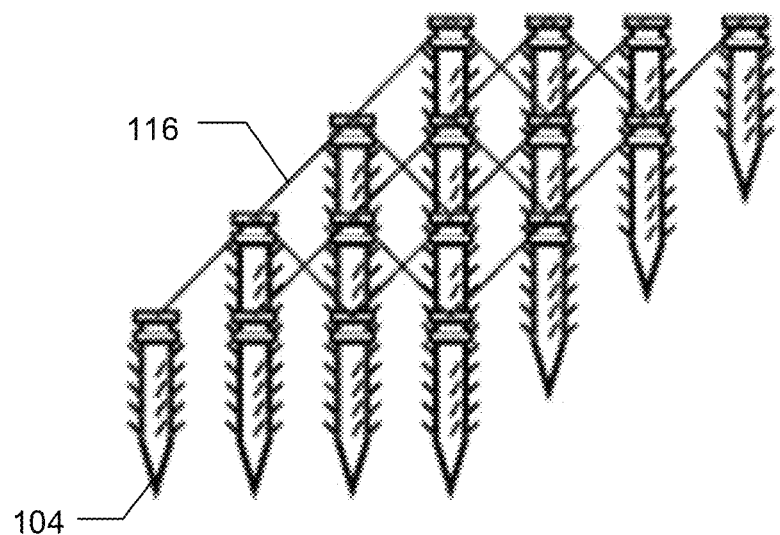
FIG. 10A shows an example of modular linked locking barbs that are linked at a single cuff.
Figure 10B:
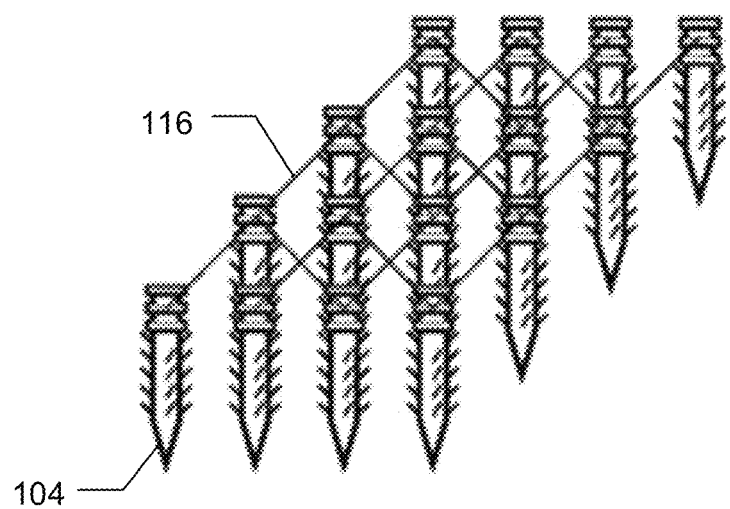
FIG. 10B shows an example of modular linked locking barbs that are linked at a double cuff.

A plurality of barbs may be linked together by a linking filament 116 connected to one or more cuffs 110 or caps 108. The linking filament 116 may connect to the top flange in a single cuff arrangement (e.g. FIG. 10A) on a barb and may connect to a middle flange in a double cuff arrangement (e.g. FIG. 10B). The linkage may allow for the plurality of barbs to pre-spaced at a set distance to be easily inserted into a plurality of apertures on the mesh by a user. The linked barbs may also allow multiple barbs to be passed through the mesh at once, in a preconfigured pattern. For instance, the barbs may come in a package of a set number of barbs (e.g. 20 barbs), being composed of two columns and ten rows of barbs at set intervals, for instance 1 cm apart from one another, and linked by plastic filaments that would allow the 20 barbs to be picked up and applied as one unit, or to be trimmed as needed and applied. The plurality of barbs may be linked in various quantities, spacing, thicknesses, lengths, angles, shapes, directions and with various projection configurations, for various indications. The cuffs or slots may be of different configurations, shapes and different angles with respect to the mesh. Alternatively, the cuffs may be in the plane of the mesh, but have mechanisms to allow the mated barbs to project at various angles. The connection between the barbs and the mesh is as rigid as possible, so that the finished barbed mesh, composed of multiple joining parts, simulates a barbed mesh where the mesh and barbs are integral. The barbs are 'locked' into the mesh once mated to it, with the intent being for the barbs to have no more individual mobility with respect to the mesh as they would if they were, in fact, materially/integrally joined with the mesh. The finished modular barbed mesh with locking barbs is therefore operable to approximate the function of the mesh with integral barbs but allow the mesh to be adapted by user assembly to conform to the needs of particular situations.

When the barbs include a flat cap, the mesh may be a large pre lattice-like mesh with apertures large enough to accommodate penetration by barbs. The mesh in this case may also be composed of woven fibers. In this example, the mesh may be placed against the tissue without fixation, and then be fixated by penetration of the mesh with barbs that do not attach themselves integrally to the mesh, but fixate the mesh by the cap on the barb. The cap may have a diameter wider than the diameter of an aperture in the mesh, such that the cap that covers the area of >1 lattice aperture, preventing the mesh from being pulled out from beneath the barbs.

In various examples, the flat cap and/or cuffs may include a rigid plastic, such as polypropylene, or metal, such as titanium or steel, to provide rigidity to the joining point of the barbs to the mesh. For cuffs made of plastic, the cuff may be formed by thickening the polymer material of the barbs. For cuffs made of metal, the metal may be sprayed on the barb or may be swaged on. The barbs may be inserted into the apertures in the linkage points of the mesh. In some examples, the apertures may be fabricated with varying depths to give increasing rigidity. The barbs may further have a flange to lock them into the apertures.

In some examples, the mesh and barbs may be integral and fabricated as one unit. For example, the mesh and barbs may be formed through injection molding or 3D printing. Alternatively, the barbs and mesh may be fabricated separately, so that different types of barbs may be mated with different meshes. The barbs and mesh and apertures may all be constructed or coated with a variety of materials, such as inert metals or dissolvable components, to alter handling characteristics and mechanical properties. Non-limiting examples include stainless steel, titanium, polypropylene, and/or polydixanone.

The barbed mesh device is operable to close tissue transcutaneously, subcutaneously, trans-fascially in the "onlay position" (e.g. superficial to the abdominal fascia), in the "sublay" or "retrorectus position," (e.g. between the rectus abdominis muscle and the posterior rectus sheath), or in the "underlay" or "intra-peritoneal position" (e.g. deep to the posterior rectus sheath). The tissues to be closed/fixated may first be temporarily approximated. For example, the edges of the opened abdominal fascia or the edges of a long skin incision may be manually approximated, or approximated by sutures, staples, or other joining devices. In some examples, the skin edges may be finely approximated with a glue such as Dermabond™ (cyanoacrylate), or with Steri-Strips™ etc. Then, the tissues may be rapidly fixated in place by placement of the barbed mesh over a broad surface area, with the incision in the center. In some examples, the mesh is pushed into place, and the barbs penetrated the underlying tissue, are retained in the tissue, and create immediate tissue positional stability (e.g. keep the wound edges together) by transmitting the tensile load from the tissues (which tend to separate) to the mesh (which is rigid in a 2-dimensional plane). For example, the barbs may penetrate the tissues with a minimal necessary mechanical force, such that the operator may merely pinch the tissues and press on the mesh to close the entire incision. In some examples, it may only take seconds to apply the mesh.

Further provided herein are methods of abdominal hernia repair or prevention using the barbed mesh. Currently, abdominal fascia is closed with sutures or meshes. Ventral hernias are similarly repaired with sutures or meshes. Sutures have inherent biomechanical problems for this application, as they may "cheesewire" through the fascia, leading to fascial dehiscence and hernia formation. Mesh overcomes this problem by allowing tissue ingrowth over a broad surface area of a strong sheet of mesh, distributing tensile strength. However, until tissue ingrowth is achieved, the mesh must be fixated using sutures. The use of sutures is time-consuming and operator-dependent. The barbed mesh with penetrating, self-adhering barbs allow the mesh to be applied to a fascial closure and achieve immediate tissue integration, without the need for any suturing.

Also provided herein are methods of skin or soft tissue closures using the barbed mesh. Currently, suturing and stapling are the standards for closing skin or soft tissue incisions. An example would be a laparotomy incision, a midline sternal incision, or an abdominoplasty incision. If an incision is long, this can be a time-consuming process. The ultimate quality of closure is dependent on the operator and can make a difference with regards to risks of complications (e.g. sternal wound dehiscence). Deeper layers of tissue are not approximated with stapling and skin suturing, unless the operator makes a specific, additional effort to do so. The barbed mesh may be used as a replacement for sutures and staples. An entire incision, including the full thickness of the subcutaneous tissue, may be closed in a matter of seconds with application of one piece of barbed mesh. This would provide tissue immobilization for healing in a rapid but stable fashion. This would also reduce the tendency towards shearing of tissue planes and dead space formation or accumulation of fluid within potential spaces.

A method of tissue closure may include approximating edges of an opened tissue (e.g. incision), placing a first side of a barbed mesh device over a broad surface area covering the edges of the opened tissue, and pressing on the device such that the barbs penetrate and are retained within the tissue. In some aspects, the method further includes drawing the other side of the barbed mesh device across the incision and pressing that side of the device into the tissues of a broad surface area across the incision from the first side. The device may be applied transcutaneously, subcutaneously, trans-fascially in the "onlay position" (e.g. superficial to the abdominal fascia), in the "sublay" or "retrorectus position," (e.g. between the rectus abdominis muscle and the posterior rectus sheath), or in the "underlay" or "intra-peritoneal position" (e.g. deep to the posterior rectus sheath).

Also provided herein is a method of closing elevated tissue planes to underlying tissues, such as an elevated flap of skin and subcutaneous tissues to the underlying fascia, using the barbed mesh, thus preventing tissue shearing and eliminating dead space for fluid collection.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A device for tissue closure, the device comprising:
  a macroporous mesh comprising a plurality of intersections each comprising an aperture, the mesh having a first side and a second side;
  a plurality of barbs extending from the plurality of intersections on the first side of the mesh, wherein each barb is received within the aperture of a respective intersection, the plurality of barbs each comprising:

a barb body; and a plurality of projections extending at an angle from the barb body; and linking filaments connected to each of the plurality of barbs, such that a set spacing between each barb may be maintained as the barbs are connected to the apertures in the mesh.

2. The device of claim 1, wherein the plurality of barbs further extend from the plurality of intersections on the second side.

3. The device of claim 2, wherein the device is operable to close tissue transcutaneously, subcutaneously, or across fascial planes.

4. The device of claim 2, wherein each of the barbs extend at an angle from 10 degrees to 170 degrees from the first side and/or the second side of the mesh.

5. The device of claim 1, wherein the plurality of barbs are operable to penetrate and self-adhere to the tissue.

6. The device of claim 1, wherein the mesh and the plurality of barbs are biologically resorbable.

7. The device of claim 1, wherein the mesh comprises at least one of polydioxanone, polypropylene, polyglecaprone, polyglactin, poly-4-hydroxybutyrate, magnesium, titanium, or other metals.

8. The device of claim 1, wherein the barbs comprises at least one of polydioxanone, polypropylene, polyglecaprone, polyglactin, poly-4-hydroxybutyrate, magnesium, titanium, or other metals.

9. The device of claim 1, wherein each of the barbs further comprises a flat cap and/or at least one circumferential cuff to secure the barb in the respective aperture.

10. The device of claim 1, wherein the mesh includes a portion without barbs.

11. The device of claim 10, wherein the mesh further comprises an elastic portion.

12. A method of tissue closure, the method comprising:

approximating edges of an opened tissue;

placing the first side of the device of claim 1 over a broad surface area covering the edges of the opened tissue; and pressing on the device, wherein the barbs penetrate and are retained within the tissue.

13. The method of claim 12, wherein the placed device is used to repair or prevent an abdominal hernia, close an incision in soft tissue, or support other methods of tissue closure to prevent dehiscence.

14. A device for tissue closure, the device comprising:

a macroporous mesh comprising a plurality of apertures, the mesh having a first side and a second side; and a plurality of barbs operable to connect to the mesh, via the apertures, and extend from at least the first side of the mesh, the plurality of barbs each comprising:

a barb body;

a plurality of projections extending at an angle from the barb body; and a flat cap and/or at least one circumferential cuff to secure each barb in a corresponding aperture, wherein the plurality of barbs are linked together, via a linking filament, prior to being connected to the apertures in the mesh, such that a set spacing between each barb may be maintained when the barbs are connected to the apertures in the mesh.

15. The device of claim 14, wherein the plurality of barbs further extend from the second side of the mesh when connected to the apertures.

16. The device of claim 15, wherein the barbs extend at an angle from 30 degrees to 90 degrees from the first side and/or the second side of the mesh, when connected to the apertures.

* * * * *